(12) United States Patent
Wetzel et al.

(10) Patent No.: US 11,761,915 B2
(45) Date of Patent: Sep. 19, 2023

(54) ESTIMATING PARAMETERS OF A FLUID

(71) Applicant: Siemens Aktiengesellschaft, Munich (DE)

(72) Inventors: Martin Wetzel, Rastatt (DE); Steffen Glöckle, Weingarten (DE); Sven Osswald, Fellbach (DE); Mike Schmanau, Malsch (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 226 days.

(21) Appl. No.: 16/918,457

(22) Filed: Jul. 1, 2020

(65) Prior Publication Data

US 2021/0003431 A1 Jan. 7, 2021

(30) Foreign Application Priority Data

Jul. 2, 2019 (EP) .................... 19183880

(51) Int. Cl.
*G01F 1/68* (2006.01)
*G01N 25/20* (2006.01)
*G01F 15/00* (2006.01)

(52) U.S. Cl.
CPC .............. *G01N 25/20* (2013.01); *G01F 1/68* (2013.01); *G01F 15/005* (2013.01)

(58) Field of Classification Search
CPC ...... G01F 1/26; G01F 15/0058; G01F 1/6847; G01F 1/68–6888; G01K 17/08; G01K 17/10; G01K 17/12; G01K 17/16; G01N 25/20

See application file for complete search history.

(56) References Cited

U.S. PATENT DOCUMENTS

| | | | | |
|---|---|---|---|---|
| 4,501,145 A | * | 2/1985 | Boegli | ............. G01F 1/6888 73/204.17 |
| 7,775,706 B1 | | 8/2010 | Feller | ..................... 374/29 |
| 9,021,878 B2 | * | 5/2015 | Grinstein | ........... G01F 1/684 73/204.11 |
| 9,841,122 B2 | | 12/2017 | Kucera et al. | |

(Continued)

FOREIGN PATENT DOCUMENTS

| | | | |
|---|---|---|---|
| CN | 105378575 A | 3/2016 | ............. F24F 11/00 |
| CN | 105402478 A | 3/2016 | ............. F16K 37/00 |

(Continued)

*Primary Examiner* — Justin N Olamit

(74) *Attorney, Agent, or Firm* — Slayden Grubert Beard PLLC

(57) ABSTRACT

A valve comprising a controller; a heater; and two temperature transducers. The controller sends a close signal to the actuator and records a first temperature signal from the first temperature transducer, then controls the heater to attain a first temperature set point at the second temperature transducer. The controller records a time or an amount of energy required to attain the first temperature set point, then sends an open signal. The controller records a second temperature, controls the heater to attain a second set point at the second transducer, and records a time or an energy required to attain the second temperature set point. The controller classifies a fluid inside based on the first value and a flow rate of the fluid through the fluid path based on the second value.

14 Claims, 5 Drawing Sheets

(56) References Cited

U.S. PATENT DOCUMENTS

| | | | |
|---|---|---|---|
| 9,874,880 B2 | 1/2018 | Thuillard et al. | |
| 9,921,588 B2* | 3/2018 | Hornung | G01F 1/74 |
| 10,007,239 B2 | 6/2018 | Burt | |
| 10,982,794 B2* | 4/2021 | Wiegand | F16K 37/0041 |
| 2014/0067135 A1 | 3/2014 | Lehnert et al. | 700/276 |
| 2015/0369644 A1* | 12/2015 | Powning | G01F 1/698 |
| | | | 73/204.18 |
| 2019/0018432 A1 | 1/2019 | Petry | G05D 7/0635 |

FOREIGN PATENT DOCUMENTS

| | | | |
|---|---|---|---|
| CN | 105531520 A | 4/2016 | F16K 31/04 |
| CN | 106 896 134 | 6/2017 | G01N 25/20 |
| DE | 10 2007 015 609 | 10/2008 | G01K 17/06 |
| EP | 3 348 923 | 7/2018 | F24F 11/00 |
| WO | 97/14763 A1 | 4/1997 | C09K 5/04 |
| WO | 98/49532 | 11/1998 | G01K 17/16 |
| WO | WO 2013/113356 * | 8/2013 | G01F 1/684 |

\* cited by examiner

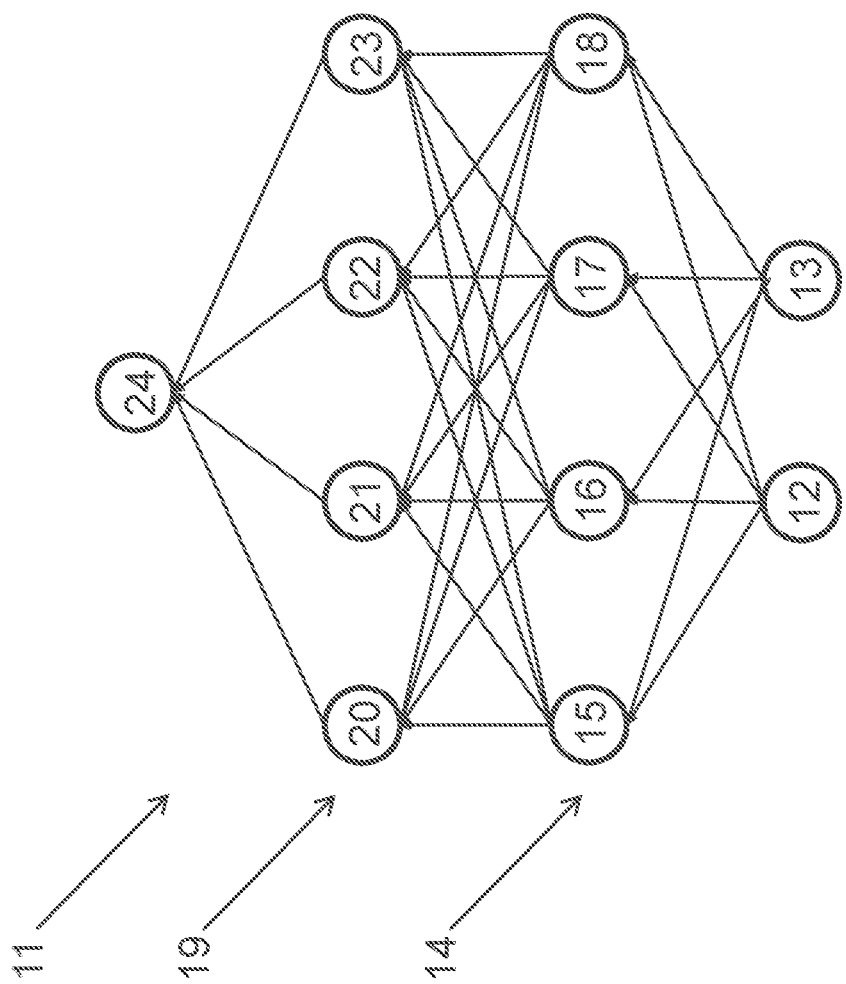

to the valve actuator (9), the open signal causing the valve actuator (9) to open the valve member (6) thereby opening the fluid path (4); record a second temperature signal from the first temperature transducer (5; 5a; 5b); produce a second temperature set point; control the heater (8) to attain the second temperature set point at the second temperature transducer (5; 5b; 5a); record a second quantity associated with controlling the heater (8) to attain the second temperature set point, the second quantity being indicative of: an amount of time required to attain the second temperature set point; or an amount of energy required to attain the second temperature set point; and employ the first quantity to classify a fluid inside and the second quantity to estimate a flow rate of the fluid through the fluid path (4).

In some embodiments, there is an inlet port (2) and an outlet port (3), wherein the fluid path (4) extends between the inlet port (2) and the outlet port (3).

In some embodiments, the heater (8), the first temperature transducer (5; 5a; 5b), and the second temperature transducer (5; 5b;5a) are situated in the fluid path (4).

In some embodiments, the controller (7) is configured to produce the first temperature set point as a function of the first temperature signal by producing a first reference temperature from the first temperature signal; and by adding a
ESTIMATING PARAMETERS OF A FLUID

CROSS-REFERENCE TO RELATED APPLICATIONS

This application claims priority to EP Application No. 19183880.4 filed Jul. 2, 2019, the contents of which are hereby incorporated by reference in their entirety.

TECHNICAL FIELD

The present disclosure relates to valves. Various embodiments may include valves enabling estimation of flow rates and/or valves enabling automated classification of fluid mixtures.

BACKGROUND

Fluid circuits such as circuits for heating, ventilation, and/or air-conditioning frequently make use of flow rate measurements. In addition to flow rates, measurements of supply temperature as well as a return temperature are required to estimate heat flux. The difference between these temperatures is assigned to a temperature drop. A quantitative measure of heat flux can then be estimated as a function of the product between flow rate and temperature drop.

An accurate estimate of heat flux requires knowledge of the specific heat of the fluid flowing through the device. That value of specific heat generally depends on the type of fluid. Circuits for heating, ventilation, and/or air conditioning commonly employ blended formulations of water and of glycol as well as blended formulations of potassium formate and water. The patent application WO97/14763A1 discloses a liquid for use in ventilation and air conditioning installations, the liquid containing 15% to 35% of potassium formate and 65% to 85% of water.

Another patent application WO98/49532A1 deals with monitoring solar plants. To that end, a measurement apparatus with temperature probes 11 and 12 is employed. A flow rate through the apparatus is determined using a flow rate sensor 20. The flow rate may also be derived from measurements of temperature rise at the locations of probes 11 and 12. WO98/49532A1 teaches determination of heat flux that accounts for the temperature dependence of specific heat.

Another patent application DE102007015609A1, describes a measurement apparatus 2 with ultrasonic transducers 4 for determining flow rates. The measurement apparatus 2 also comprises a pair of temperature probes 9 for recording the temperature drop between the supply end and the return end. The temperature probes 9 as well as the ultrasonic flow rate sensors 4 connect to a controller 12.

The measurement apparatus 2 of DE102007015609A1 provides a micro-anemometer 13. The micro-anemometer 13 is arranged in between the supply end and the return end and also connects to the controller 12. An estimate k related to specific heat is obtained from the values recorded by the micro-anemometer 13. The micro-anemometer 13 thus allows values of k to be factored into an estimate of heat flux. In DE102007015609A1, paragraph 48, a temperature rise is recorded as a function of a predetermined amount of power supplied to a heater 15. DE102007015609A1 does not teach recording an amount of power as a function of a predetermined temperature rise.

U.S. Pat. No. 7,775,706 B1 teaches a compensated heat energy meter. The meter according to U.S. Pat. No. 7,775,706 B1 comprises a flow sensor 16 as well as an inlet temperature sensor 20 and an outlet temperature sensor 22. U.S. Pat. No. 7,775,706 B1 discloses a meter operable to measure specific heat of a working fluid.

A patent application CN106896134A deals with a dual-medium supercritical low-temperature thermal performance test platform.

A patent application US2019/018432A1 teaches control gain automation.

A patent application EP3348923A1 deals with system for cooling a room. EP3348923A1 also deals with a valve assembly.

SUMMARY

The teachings of the instant disclosure may be used in valves for heating, ventilation, and/or air-conditioning installations. The valves may be used to classify fluids for a wide range of liquids employed in heating, ventilation and/or air-conditioning installations, such as a water-glycol mixture flowing through a tempering circuit. For example, some embodiments of the teachings herein include a valve (1) comprising a controller (7), a fluid path (4), a valve member (6) situated in the fluid path (4); the valve member (6) being selectively movable between a closed position which closes the fluid path (4) and an open position which opens the fluid path (4); the valve (1) comprising a valve actuator (9) coupled to the valve member (6); the valve (1) comprising a heater (8), a first (5; 5a; 5b) and a second (5; 5b; 5a) temperature transducer; the controller (7) being in operative communication with the valve actuator (9), with the heater (8) and with the temperature transducers (5; 5a, 5b) and being configured to: send a close signal to the valve actuator (9), the close signal causing the valve actuator (9) to close the valve member (6) thereby closing the fluid path (4); record a first temperature signal from the first temperature transducer (5; 5a; 5b); produce a first temperature set point; control the heater (8) to attain the first temperature set point at the second temperature transducer (5; 5b; 5a); record a first quantity associated with controlling the heater (8) to attain the first temperature set point, the first quantity being indicative of: an amount of time required to attain the first temperature set point; or an amount of energy required to attain the first temperature set point; and send an open signal first predetermined increment to the first reference temperature to produce the first temperature set point; and wherein the controller (7) is configured to produce the second temperature set point as a function of the second temperature signal by producing a second reference temperature from the second temperature signal; and by adding a second predetermined increment to the second reference temperature to produce the second temperature set point.

In some embodiments, the controller (7) is configured to: record a first feedback signal from the second temperature transducer and control the heater (8) based on the first feedback signal to attain the first temperature set point at the second temperature transducer (5; 5b; 5a); and after sending the open signal to the valve actuator (9): record a second feedback signal from the second temperature transducer and control the heater (8) based on the second feedback signal to attain the second temperature set point at the second temperature transducer (5; 5b; 5a).

In some embodiments, the controller (7) is configured to: record a first feedback temperature signal from the second temperature transducer (5; 5b; 5a); produce a first error signal as a function of the first temperature set point and of the first feedback temperature signal; produce a first control output signal as a function of the first error signal, the first control output signal being indicative of a first amount of energy to be dissipated by the heater (8); transmit the first control output signal to the heater (8); and after sending the open signal to the valve actuator (9): record a second feedback temperature signal from the second temperature transducer (5; 5b; 5a); produce a second error signal as a function of the second temperature set point and of the second feedback temperature signal; produce a second control output signal as a function of the second error signal, the second control output signal being indicative of a second amount of energy to be dissipated by the heater (8); and transmit the second control output signal to the heater (8).

In some embodiments, the controller (7) is configured to: control the heater (8) to attain the first temperature set point at the second temperature transducer (5; 5b; 5a) by recording a first feedback signal from the second temperature transducer (5; 5b; 5a); and by producing a first feedback temperature from the first feedback signal; and by determining if the first feedback temperature is within a first predetermined margin from the first temperature set point; if the first feedback temperature is within the first predetermined margin from the first temperature set point: record a first quantity associated with controlling the heater (8), the first quantity being indicative of: an amount of time required to attain the first temperature set point; or an amount of energy required to attain the first temperature set point; and after sending the open signal to the valve actuator (9): control the heater (8) to attain the second temperature set point at the second temperature transducer (5; 5b; 5a) by recording a second feedback signal from the second temperature transducer (5; 5b; 5a); and by producing a second feedback temperature from the second feedback signal; and by determining if the second feedback temperature is within a second predetermined margin from the second temperature set point; if the second feedback temperature is within the second predetermined margin from the second temperature set point: record a second quantity associated with controlling the heater (8), the second quantity being indicative of: an amount of time required to attain the second temperature set point; or an amount of energy required to attain the second temperature set point.

In some embodiments, the controller (7) is configured to: send a close signal to the valve actuator (9), the close signal causing the valve actuator (9) to close the valve member (6) thereby closing the fluid path (4); and at least one second after sending the close signal, record a first temperature signal from the first temperature transducer (5; 5a; 5b).

In some embodiments, the controller (7) is configured to: send a close signal to the valve actuator (9), the close signal causing the valve actuator (9) to close the valve member (6) thereby closing the fluid path (4); receive a first confirmation signal from the valve actuator (9), the first confirmation signal indicating that the fluid path (4) is closed; and at least one second after receiving the first confirmation signal, record a first temperature signal from the first temperature transducer (5; 5a; 5b).

In some embodiments, the controller (7) is configured to: send an open signal to the valve actuator (9), the open signal causing the valve actuator (9) to open the valve member (6) thereby opening the fluid path (4); and at least one second after sending the open signal, record a second temperature signal from the first temperature transducer (5; 5a; 5b).

In some embodiments, the controller (7) is configured to: send an open signal to the valve actuator (9), the open signal causing the valve actuator (9) to open the valve member (6) thereby opening the fluid path (4); receive a second confirmation signal from the valve actuator (9), the second confirmation signal indicating that the fluid path (4) is open; and at least one second after receiving the second confirmation signal, record a second temperature signal from the first temperature transducer (5; 5a; 5b).

In some embodiments, the valve (1) comprises an inlet port (2) and an outlet port (3), the inlet port (2) and the outlet port (3) defining an upstream direction from the outlet port (3) to the inlet port (2); the valve (1) further comprising a first thermoresistive device (10a) situated in the fluid path (4); wherein the first thermoresistive device (10a) comprises a first housing and comprises the heater (8) and comprises the first temperature transducer (5a); wherein the heater (8) and the first temperature transducer (5a) are situated inside the first housing; and wherein the first thermoresistive device (10a) is situated upstream of the second temperature transducer (5b).

In some embodiments, the valve (1) comprises an inlet port (2) and an outlet port (3), the inlet port (2) and the outlet port (3) defining a downstream direction from the inlet port (2) to the outlet port (3); the valve (1) further comprising a second thermoresistive device (10b) situated in the fluid path (4); wherein the second thermoresistive device (10b) comprises a second housing and comprises the heater (8) and comprises the second temperature transducer (5b); wherein the heater (8) and the second temperature transducer (5b) are situated inside the second housing; and wherein the second thermoresistive device (10b) is situated downstream of the first temperature transducer (5a).

As another example, some embodiments include a method of estimating parameters of a fluid, the method comprising the steps of: sending a close signal to a valve actuator (9) of a valve (1), the close signal causing the valve actuator (9) to close a valve member (6) situated in a fluid path (4) of the valve (1) thereby closing the fluid path (4); recording a first temperature signal from a first temperature transducer (5; 5a; 5b) situated in the fluid path (4); producing a first temperature set point as a function of the first temperature signal; controlling a heater (8) situated in the fluid path (4) to attain the first temperature set point at a second temperature transducer (5; 5b; 5a) situated in the fluid path (4); recording a first quantity associated with controlling the heater (8) to attain the first temperature set point, the first quantity being indicative of: an amount of time required to attain the first temperature set point; or an amount of energy required to attain the first temperature set point; and sending an open signal to the valve actuator (9), the open signal causing the valve actuator (9) to open the valve member (6) thereby opening the fluid path (4); recording a second temperature signal from the first temperature transducer (5; 5*a*; 5*b*); producing a second temperature set point as a function of the second temperature signal; controlling the heater (8) to attain the second temperature set point at the second temperature transducer (5; 5*b*; 5*a*); recording a second quantity associated with controlling the heater (8) to attain the second temperature set point, the second quantity being indicative of: an amount of time required to attain the second temperature set point; or an amount of energy required to attain the second temperature set point; and employing the first quantity to classify the fluid inside the fluid path (4) and employing the second quantity to estimate a flow rate of the fluid through the fluid path (4).

As another example, some embodiments include a tangible machine-readable medium having a set of instructions stored thereon that when executed by one or more processors cause the one or more processors to perform a method as described herein.

BRIEF DESCRIPTION OF THE DRAWINGS

Various features will become apparent to those skilled in the art from the following detailed description of the disclosed non-limiting embodiments. The drawings that accompany the detailed description can be briefly described as follows:

FIG. 5 shows a neural network for fluid classification incorporating teachings of the instant disclosure.

DETAILED DESCRIPTION

Figure 1:
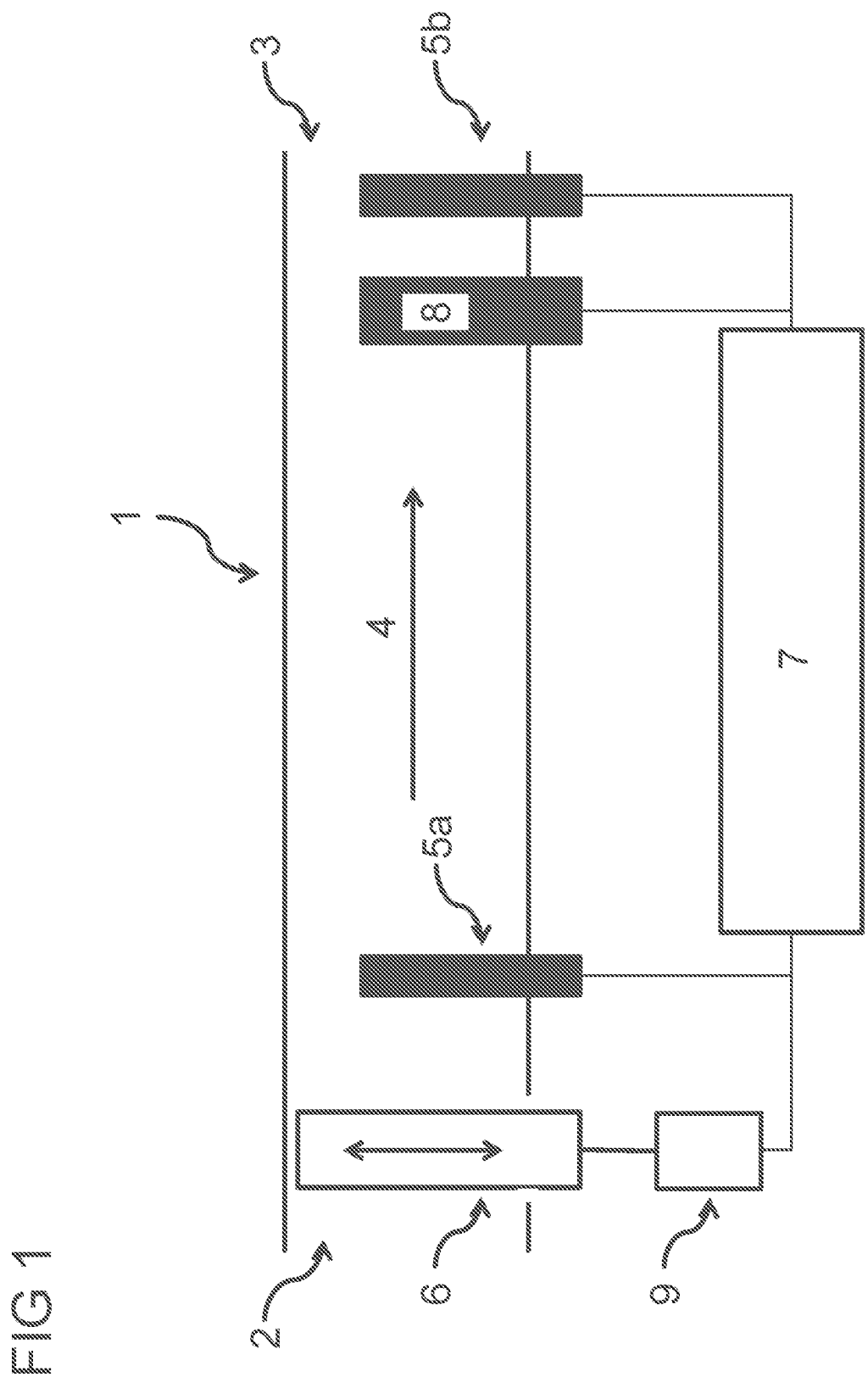
FIG. 1 is a schematic view of a valve incorporating teachings of the instant disclosure.

Various valves incorporating the teachings herein provide an estimate of a flow rate of the fluid. Rather than using separate transducers to classify a fluid and flow rate, the valve harnesses the same set of transducers for the two measurements. To that end, a valve member such as a piston and/or a plug closes. The closed valve member yields zero flow. A classification of the fluid is then carried out using an anemometer. The valve member afterwards opens. The same anemometer is then employed to estimate a flow rate.

Various embodiments of the teachings of the instant disclosure include a valve comprising a controller, a fluid path, a valve member situated in the fluid path; the valve member being selectively movable between a closed position which closes the fluid path and an open position which opens the fluid path; the valve comprising a valve actuator coupled to the valve member; the valve comprising a heater, a first and a second temperature transducer; the controller being in operative communication with the valve actuator, with the heater and with the temperature transducers and being configured to:

send a close signal to the valve actuator, the close signal causing the valve actuator to close the valve member thereby closing the fluid path;

record a first temperature signal from the first temperature transducer;

produce a first temperature set point;

control the heater to attain the first temperature set point at the second temperature transducer;

record a first quantity associated with controlling the heater to attain the first temperature set point, the first quantity being indicative of:

an amount of time required to attain the first temperature set point; or an amount of energy required to attain the first temperature set point; and send an open signal to the valve actuator, the open signal causing the valve actuator to open the valve member thereby opening the fluid path;

record a second temperature signal from the first temperature transducer;

produce a second temperature set point;

control the heater to attain the second temperature set point at the second temperature transducer;

record a second quantity associated with controlling the heater to attain the second temperature set point, the second quantity being indicative of:

an amount of time required to attain the second temperature set point; or an amount of energy required to attain the second temperature set point; and employ the first quantity to classify a fluid such as a water-glycol mixture inside the fluid path and employ the second quantity to estimate a flow rate of the fluid through the fluid path.

Some additional embodiments include a method of estimating parameters of a fluid, the method comprising the steps of: sending a close signal to a valve actuator of a valve, the close signal causing the valve actuator to close a valve member situated in a fluid path of the valve thereby closing the fluid path;

recording a first temperature signal from a first temperature transducer situated in the fluid path;

producing a first temperature set point as a function of the first temperature signal;

controlling a heater situated in the fluid path to attain the first temperature set point at a second temperature transducer situated in the fluid path;

recording a first quantity associated with controlling the heater to attain the first temperature set point, the first quantity being indicative of:

an amount of time required to attain the first temperature set point; or an amount of energy required to attain the first temperature set point; and sending an open signal to the valve actuator, the open signal causing the valve actuator to open the valve member thereby opening the fluid path;

recording a second temperature signal from the first temperature transducer;

producing a second temperature set point as a function of the second temperature signal;

controlling the heater to attain the second temperature set point at the second temperature transducer;

recording a second quantity associated with controlling the heater to attain the second temperature set point, the second quantity being indicative of:
- an amount of time required to attain the second temperature set point; or
- an amount of energy required to attain the second temperature set point; and employing the first quantity to classify the fluid such as a water-glycol mixture inside the fluid path and employing the second quantity to estimate a flow rate of the fluid through the fluid path.

In some embodiments, a valve and a method of estimating parameters of a fluid classify a mixture contained in a tempering circuit during installation and/or during commissioning. In some embodiments, a valve and a method of estimating parameters of a fluid enables an assessment of chemical and/or physical degradation of a mixture contained in a tempering circuit. In some embodiments, a valve and a method of estimating parameters of a fluid classifies a mixture while the mixture is not circulating in the tempering circuit. In some embodiments, a valve and a method of estimating parameters of a fluid classifies a mixture while the mixture is circulating in the tempering circuit. In some embodiments, a valve and a method of estimating parameters of a fluid can be retro-fitted to and/or applied to existing installations.

Various embodiments of the teachings herein include a valve that is part of an installation for heating, ventilation and/or air conditioning. In some embodiments, a plurality of such valves is arranged in an installation for heating, ventilation and/or air conditioning.

The valve 1 as shown in FIG. 1 has an inlet port 2 and an outlet port 3. One of ordinary skill in the art upon reviewing this disclosure understands that the valve 1 is not limited to a single inlet port 2 and is not limited to a single outlet port 3. The valve 1 can actually provide a plurality of inlets ports and/or a plurality of outlet ports. A fluid path 4 extends from the inlet port 2 to the outlet port 3 of the valve 1.

Inlet port 2 provides a supply end for supply of a fluid to the valve 1. Likewise, outlet port 3 provides a return end. A fluid such as water and/or a blend thereof, e.g., a blend of water and of at least one compound selected from:
- calcium chloride,
- ethanol,
- ethylene glycol,
- glycerol,
- magnesium chloride,
- methanol,
- potassium acetate,
- potassium formate,
- propylene glycol, or
- sodium chloride enters the valve 1 via inlet port 2 and leaves via outlet port 3. The fluid entering via inlet port 2 and leaving via outlet port 3 may be a combustible fluid and/or:
- R-401A,
- R-404A,
- R-406A,
- R-407A,
- R-407C,
- R-408A,
- R-409A,
- R-410A,
- R-438A,
- R-500, or
- R-502 refrigerant. The above lists are not exhaustive.

In some embodiments, a first temperature transducer 5a is arranged at or near the inlet port 2. The first temperature transducer 5a functions to record a signal indicative of a supply temperature at or near the supply end of the valve 1. A second temperature transducer 5b is arranged at or near the outlet port 3. The second temperature transducer 5b functions to record a signal indicative of a return temperature at or near the return end of the valve 1. It is envisaged that at least one of the temperature transducers 5a, 5b is or comprises a PT100 element and/or at PT1000 element and/or a negative thermal coefficient (NTC) element and/or a positive thermal coefficient (PTC) element. It is also envisaged that a fibre optical sensor is employed to record a signal indicative of temperature.

A valve member 6 is arranged at or near the fluid path 4. The valve member 6 is selectively movable between a closed position of the fluid path 4 and an open position of the fluid path 4. The closed position closes the fluid path 4 between the inlet port 2 and the outlet port 3. The closed position of the valve member 6 thus obturates fluid flow through the fluid path 4. The open position opens the fluid path 4 between the inlet port 2 and the outlet port 3. The open position of the valve member 6 enables fluid flow through the fluid path 4. In an embodiment, the valve member 6 is movable between the closed position of the fluid path 4 and the open position of the fluid path 4.

The valve member 6 mechanically couples to a valve actuator 9 such as a solenoid actuator. The valve actuator 9 functions to selectively move the valve member 6 between the closed position of the valve member 6 and the open position of the valve member 6. In an embodiment, the valve actuator 9 moves the valve member 6 between the closed position of the valve member 6 and the open position of the valve member 6.

A controller 7 communicatively couples to the temperature transducers 5a, 5b and to the valve actuator 9. It is also envisaged that the controller 7 is in operative communication with the valve member 6. The controller 7 can, by way of non-limiting example, be in operative communication with the valve member 6 via a limit switch and/or via a microswitch. The controller 7 can then read a position of the valve member 6 from the limit switch and/or from the microswitch.

In some embodiments, the controller 7 is or comprises a microprocessor. In some embodiments, controller 7 is or comprises a microcontroller. The controller 7 also provides a processing unit such as an arithmetic logic unit. It is envisaged that the processing unit such as the arithmetic logic unit is an integral part of the controller 7. That is, the controller 7 and its processing unit are arranged in the same chip, preferably on the same system on a chip (SoC).

The connections between the transducers 5a, 5b and the controller 7 are at least unidirectional. The controller 7 is thus operable to read signals originating from these transducers 5a, 5b. Unidirectional connections confer advantages in terms of reduced system complexity.

The connection between the controller 7 and the valve actuator 9 is at least unidirectional. The controller 7 is thus operable to send signals to the actuator 9. Unidirectional connections confer advantages in terms of reduced system complexity.

In some embodiments, controller 7 provides one analog-to-digital converter or several analog-to-digital converters that change analog readings obtained from the transducers 5a, 5b into digital representations of these readings. In some embodiments, at least one analog-to-digital converter of controller 7 provides delta-sigma modulation. In some embodiments, an analog-to-digital converter with delta-sigma modulation reduces the noise of signals obtained from the transducers 5a, 5b.

In some embodiments, at least one of these analog-to-digital converters, in particular at least one analog-to-digital converter providing delta-sigma modulation, is an integral part of the controller 7. That is, the controller 7 and at least one analog-to-digital converter, in particular at least one analog-to-digital converter providing delta-sigma modulation, are arranged on the same chip, e.g., on the same system on a chip (SoC). Controllers 7 with integrated analog-to-digital converters such as controllers having integrated analog-to-digital converter providing delta-sigma modulation yield more compact solutions.

In some embodiments, the connection between the controller 7 and the valve actuator 9 is bidirectional. The controller 7 is thus operable to read position signals indicative of positions from the valve actuator 9. These position signals can, by way of non-limiting example, be indicative of a position of the valve actuator 9 and/or be indicative of a closed position of the valve member 6 and/or be indicative of an open position of the valve member 6. Bidirectional connections afford greater flexibility.

The processing unit and the analog-to-digital converter(s) enable the controller 7 to process signals indicative of temperature into measures of temperature. The processing unit and the analog-to-digital converter(s) also enable the controller 7 to process position signals into measures of position.

A heater 8 is arranged in the fluid path 4 adjacent the return temperature transducer 5b. That is, the heater 8 is arranged at or near the outlet port 3 of the valve 1. In some embodiments, the heater 8 is a hot-wire device. In some embodiments, a light source such as a laser is employed to supply the heater 8 with power. The heater 8 is also communicatively coupled to the controller 7. The connection between heater 8 and controller 7 is at least unidirectional. The controller 7 is thus operable to transmit signals to the heater 8. A unidirectional connection from the controller 7 to the heater 8 confers advantages in terms of reduced complexity.

With the heater 8 being a hot-wire device, the controller 7 can comprise a digital-to-analog converter. The digital-to-analog converter changes a digital signal into an electric current to be supplied to the hot-wire device 8. In some embodiments, the digital-to-analog converter is an integral component of the controller 7. That is, the digital-to-analog converter and the controller 7 are arranged in the same chip, preferably on the same system on a chip (SoC).

Given that the resistivity R of the hot-wire device 8 is ohmic, the hot-wire device 8 will dissipate an amount of power $P_{el}$ that is proportional to the square of the electric current I through the hot-wire device 8:

$$P_{el}=R\times I^2$$

An amplifier such as an operational amplifier can be employed to suitably amplify the electric current produced by the digital-to-analog converter. That amplifier would typically be connected in between the digital-to-analog converter and the hot-wire device 8.

The controller 7 can as well produce a pulse-width modulated signal to drive an electric current through the heater 8. An amplifier such as an operational amplifier can again be employed to suitably amplify the pulse-width modulated electric current produced by the controller 7. That amplifier would typically be connected in between the digital-to-analog converter and the hot-wire device 8.

The arrangement shown on FIG. 1 enables an estimate of thermal conductivity λ and/or of specific heat capacity in accordance with a first approach. This measurement of thermal conductivity λ and/or of specific heat capacity is derived from a technique known as constant temperature anemometry (CTA). Constant temperature anemometry is based on a constant temperature of a temperature probe such as transducer 5b. An amount of heat dissipated by the heater 8 is thus controlled to maintain a constant temperature recorded by transducer 5b. According to an aspect, the controller employs proportional and integral (PI) or proportional and integral and derivative (PID) control to maintain a set point at the transducer 5b. The skilled person derives suitable proportional, integral and/or derivative parameter when implementing the control loop. It is envisaged that the skilled person employs self-adaptive control to maintain constant temperature at the transducer 5b.

An estimate of heat conductivity λ(T) and/or of specific heat capacity requires at least two recordings of constant, but different, temperatures $T_1$ and $T_2$ at the location of the transducer 5b. A value of heat conductivity λ(T) can then be estimated using the relationship between dissipated power P and a temperature drop across the heater $\Delta T_8$ $$P=\lambda(T)\times(a+b\times Pr^{0.33}\times v^{-0.5}\times v^{0.5}\times K)\times \Delta T_8,$$

$$K=(Pr_F/Pr_W)^{0.25}$$

wherein a and b and K are constants, Pr denotes the Prandtl number, v denotes kinematic viscosity, $Pr_F$ denotes the Prandtl number of the fluid at fluid temperature, and $Pr_W$ denotes the Prandtl number of the fluid at the temperature of a housing.

Thermal conductivity λ(T) and/or specific heat capacity are advantageously determined at zero fluid velocity, i.e. v=0. To that end, the valve member 6 is moved to the closed position. The above relationship then reads $$P=\lambda(T)\times a\times \Delta T_8.$$

In some embodiments, the temperature at the location of the transducer 5b is kept constant during at least one second, during at least two seconds, and/or during at least five seconds. Long durations at temperatures $T_1$ and $T_2$ yield more accurate values of dissipated power and hence more accurate values of thermal conductivity λ(T) and/or of specific heat capacity. Ideally, the same durations apply whilst recording the first temperature $T_1$ and the second temperature $T_2$. In an embodiment, temperatures $T_1$ and $T_2$ are kept constant within ±0.5 Kelvin, within ±0.2 Kelvin, and/or within ±0.1 Kelvin.

In some embodiments, the system may record power consumption at more than two constant, but different, temperatures $T_1$ and $T_2$. Values of power consumption can, by way of non-limiting example, be recorded at five constant, but mutually different, temperatures or even at ten constant, but mutually different, temperatures. Higher numbers of recorded values yield more accurate estimates of heat conductivity λ(T). In some embodiments, an estimate of heat conductivity λ(T) is determined by regression analysis such as by linear regression analysis.

A second approach to estimating heat conductivity λ(T) and/or of specific heat capacity leverages differences in boiling temperature of a mixture of fluids. The second approach resembles a technique known as differential scanning calorimetry (DSC). In a mixture of two fluids W and G with different boiling points $T_W$ and $T_G$, the controller 7 raises the output of the heater 8. The output of the heater 8 increases until a signal from the temperature transducer 5b indicates that one of the boiling points $T_W$ or $T_G$ is reached. As the temperature of the mixture approaches the lower of the boiling points $T_W$ and $T_G$, power dissipation increases disproportionately with temperature. That disproportionate increase in power dissipation is caused by the vaporization enthalpy of the fluid that corresponds to the lower of the boiling points $T_W$ and $T_G$. The disproportionate increase in power dissipated by the heater 8 is also proportional to the amount of fluid with the lower of the boiling points $T_W$ and $T_G$. The relative content of the fluid with the lower of the boiling points $T_W$ and $T_G$ can thus be estimated from an increase in power dissipated by the heater 8 at the respective boiling point.

In some embodiments, the valve 1 comprises an additional pressure transducer. Since the boiling point of a fluid generally depends on pressure, the additional pressure transducer can be employed to improve on the accuracy of the measurement.

In some embodiments, the fluid is a binary mixture of water and of ethylene glycol. Water at atmospheric pressure of 1013 hPa exhibits a boiling point of $T_W$=373 K. Ethylene glycol at atmospheric pressure of 1013 hPa exhibits a boiling point of $T_G$=470 K. Accordingly, the lower of the two boiling points is reached at 373 K. The power output of heater 8 thus increases until a signal from the temperature probe 5b indicates or approaches a temperature of 373 K. A disproportionate increase in power dissipated by the heater 8 with temperature can then be registered due to the vaporization enthalpy of water. Finally, that increase in dissipated power is mapped to the content of water in the binary mixture of water and of ethylene glycol.

A third approach to estimating heat conductivity $\lambda(T)$ and/or specific heat capacity works similar to temperature rise tests of power apparatuses such as power transformers. The approach is based on the physical properties of the heat equation $$\frac{dT}{dt} = \frac{\lambda}{c_p \times \rho} \nabla^2 T,$$

wherein $c_p$ denotes specific heat capacity and $\rho$ denotes mass density. This partial differential equation describes the spatial ($\nabla^2$) and temporal ($d/dt$) distribution of temperature T in a fluid with thermal conductivity $\lambda(T)$, with specific heat $c_p$ and with mass density $\rho$. The coefficient $$\alpha = \frac{\lambda}{c_p \times \rho} = \frac{1}{R \times c_p \times \rho}$$

is also known as thermal diffusivity. The thermal conductivity $\lambda(T)=1/R$ determines the response in the time domain of the system to dynamic impulse. In other words, the inverse R of thermal conductivity $\lambda(T)$ plays a role similar to the role of a resistor in a resistive capacitive RC circuit. The system thus exhibits attenuating behaviour in response to a (dynamic) impulse. A (dynamic) impulse can, by way of non-limiting example, be produced by modulating an over-temperature of heater 8.

In some embodiments, a given amount of output power is applied to the heater 8. At least two, preferably at least five, yet more preferably at least ten temperature signals $T_i$ are then recorded at the transducer 5b together with their respective time values $t_i$. A curve of temperature T versus time t $$T(t) = T_0 \times \exp(-t/\alpha)$$

is fitted to the temperature signals $T_i$ recorded at time values $t_i$. The curve fit produces an estimate of a constant $T_0$ as well as an estimate of thermal diffusivity $\alpha$. The value of thermal diffusivity $\alpha$ can be looked up in a lookup table and be mapped to a blend of fluids. Alternatively, a particular blend of fluids is determined from thermal diffusivity $\alpha$ using linear interpolation. Also, thermal diffusivity $\alpha$ affords an estimate of specific heat capacity for a given value of heat conductivity. Likewise, thermal diffusivity affords an estimate of heat conductivity for a given value of specific heat capacity.

Figure 2:
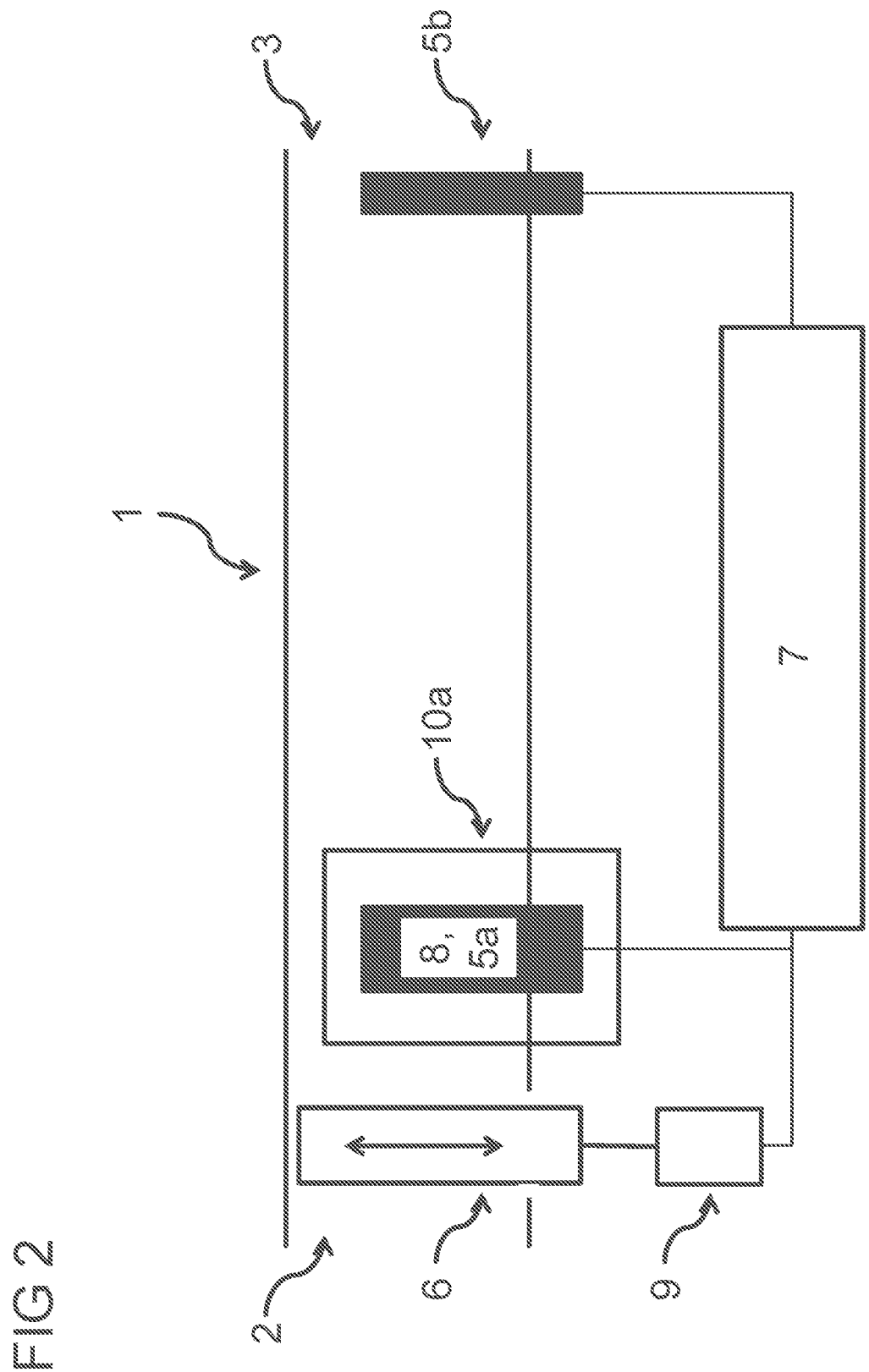
FIG. 2 provides a schematic view of a valve incorporating teachings of the instant disclosure with a heater element disposed near a supply end.

Now turning to FIG. 2, a valve 1 is depicted with a heater 8 disposed at or near the inlet port 2 of the valve 1. Accordingly, the heater 8 is arranged in the fluid path 4 adjacent the supply temperature transducer 5a. In some embodiments, the heater 8 is a hot-wire device. In some embodiments, a light source such as a laser is employed to supply the heater 8 with energy. The heater 8 and the temperature transducer 5a may be arranged inside a common housing thereby forming a thermoresistive device 10a.

Figure 3:
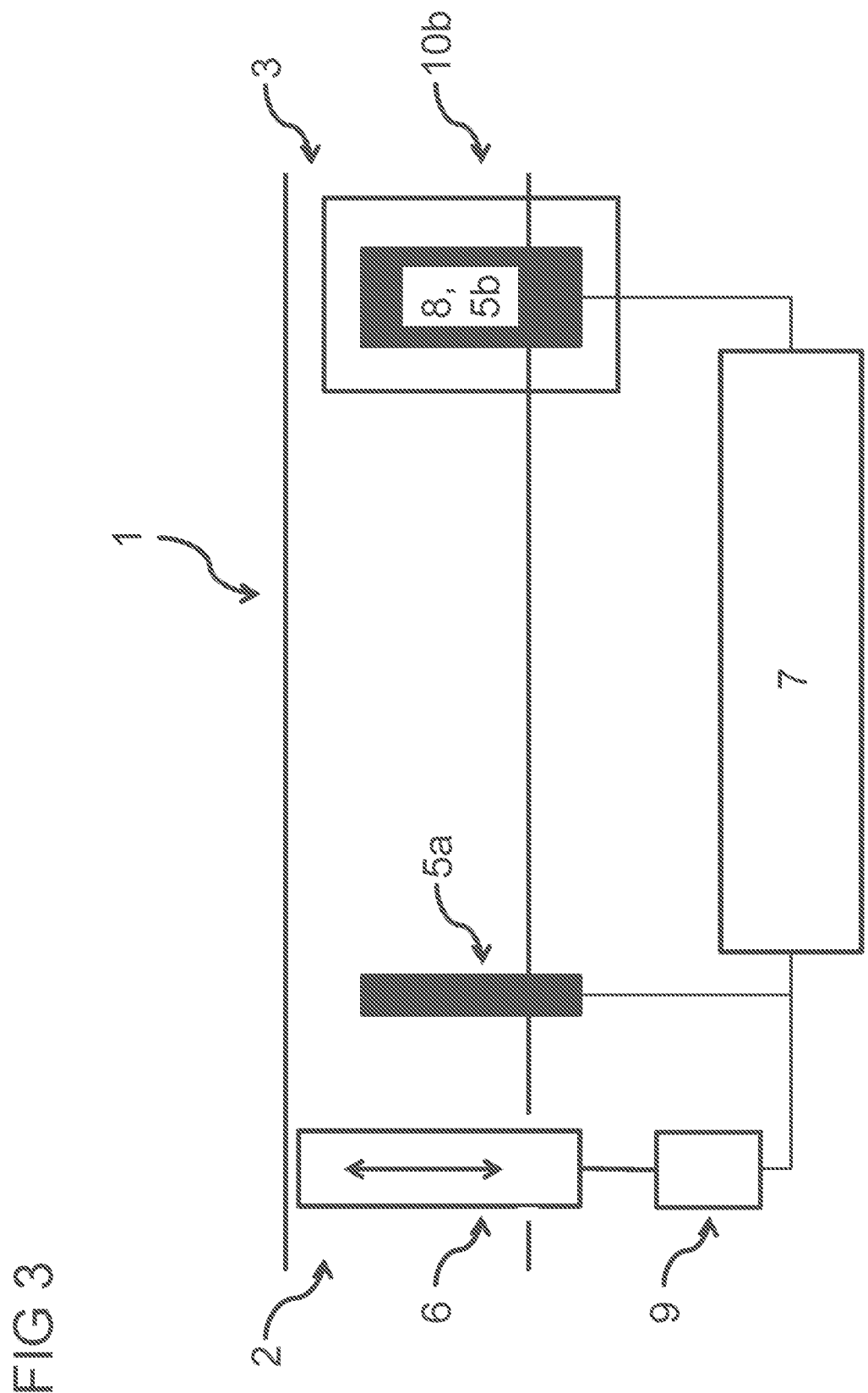
FIG. 3 provides a schematic view of a valve incorporating teachings of the instant disclosure with a heater element disposed near a return end.

Now referring to FIG. 3, a valve 1 is shown with a heater 8 and a return temperature transducer 5b inside a common housing thereby forming a thermoresistive device 10b. An aperture may enable fluid communication between the inside of the housing and the fluid path 4 extending between the inlet port 2 and the outlet port 3. The housing as shown on FIG. 3 provides an upstream side pointing in the direction of inlet port 2. The housing also provides a downstream side pointing in the direction of outlet port 3. The at least one aperture may be arranged on the downstream side of the housing. That is, the aperture points in the direction of outlet port 3. An aperture arranged on the downstream side of the housing inhibits ingress of particles into the housing. Particles dissolved in the fluid flowing through the fluid path 4 bypass the housing rather than enter inside the housing via downstream aperture.

In some embodiments, the at least one aperture provides a diameter dimension of one millimeter, of 0.5 millimeters, and/or of 0.2 millimeters. Small diameters may confer advantages in terms of isolation the inside of the housing from particles and/or from turbulence.

In some embodiments, the at least one aperture is a through-hole, a cylindrical through-hole. A cylindrical or substantially cylindrical aperture confers benefits in terms of low manufacturing cost since such apertures can be manufactured via drilling. In some embodiments, the at least one aperture provides a quadratic, a rectangular or a polygonal cross-section. The inside of the housing ideally is in fluid communication with the fluid path 4. Yet, the inside of the housing is also substantially isolated from other portions of the fluid path 4. That way, fluid velocity inside the housing is reduced to zero or to substantially zero. In other words, any impact of fluid velocity v on the result of fluid classification is largely inhibited.

Figure 4:
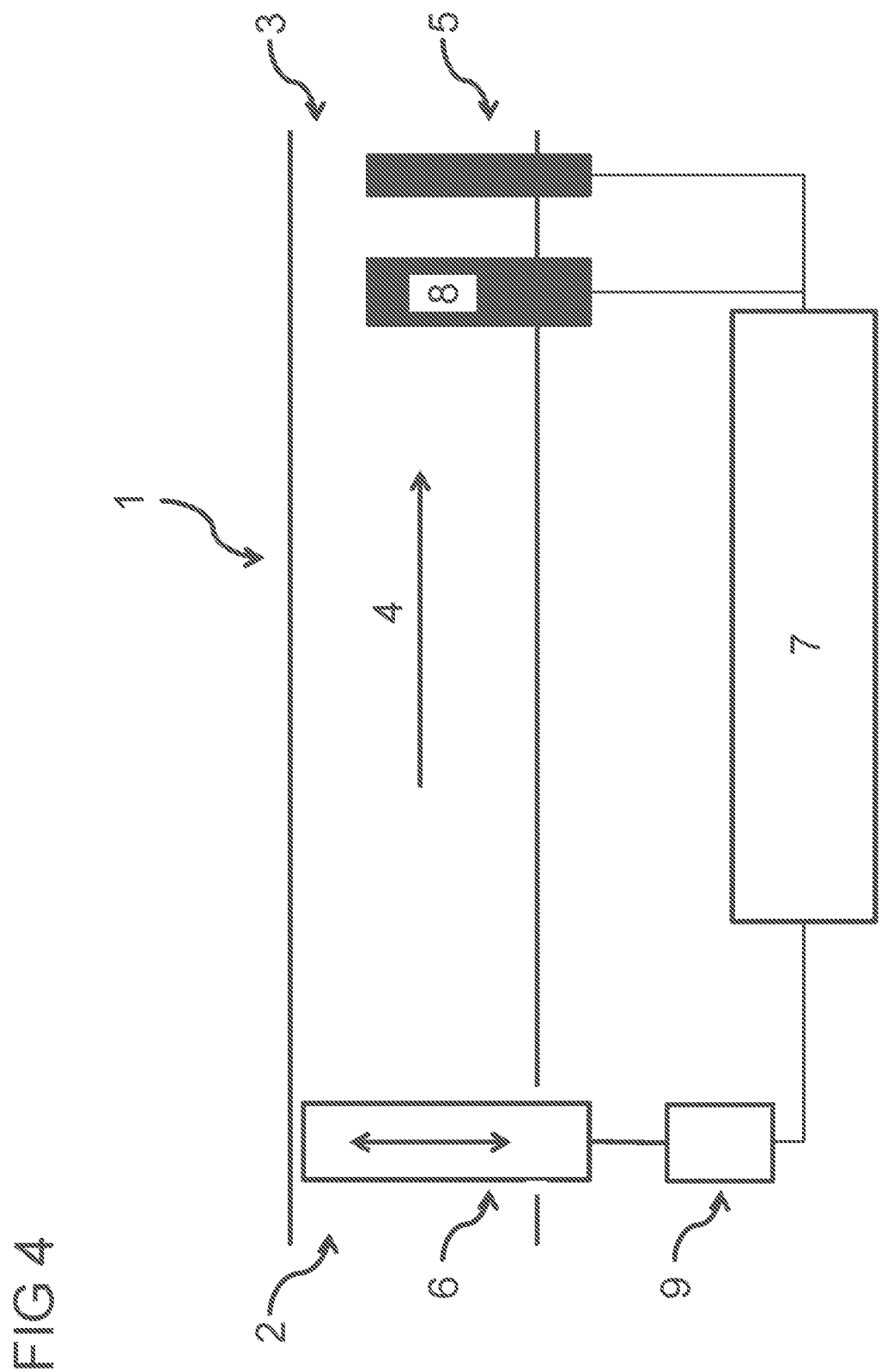
FIG. 4 provides a schematic view of a valve incorporating teachings of the instant disclosure with a single temperature transducer.

In some embodiments, the aperture comprises a filter. The filter improves on isolation of the inside of the housing from other portions of the fluid path 4. The temperature transducers 5a, 5b can also be combined. That is, there is one temperature transducer rather than two temperature transducers 5a, 5b adjacent the inlet port 2 and the outlet port 3. A single temperature transducer such as the temperature transducer 5 shown on FIG. 4 is then employed. It is envisaged to arrange the heater 8 and the temperature transducer 5 inside a common housing.

In some embodiments, the controller 7 implements a neural network such as the network 11 shown in FIG. 5. The neural network 11 comprises at least an input neuron 12 that corresponds to (is associated with) a value of dissipated heat. The neural network 11 also comprises at least an input neuron 13 that corresponds to (is associated with) a value indicative of temperature. It is envisaged that the neural network 11 comprises additional input neurons for historical values of dissipated heat and/or temperature.

Any input to the neural network 11 is ideally normalized. The neural network 11 also comprises an output neuron 24 indicative of fluid type. In some embodiments, a value produced by output neuron of 0 indicates the fluid is water whilst an output value of 1 indicates the fluid is ethylene glycol. In some embodiments, the neural network 11 comprises separate output neurons for water content and for (ethylene) glycol content.

In some embodiments, the output neuron 24 indicates a specific heat capacity of a fluid inside the fluid path 4. In some embodiments, the output neuron 24 indicates a value of heat conductivity of a fluid inside the fluid path 4. In some embodiments, the neural network provides a first output neuron indicative of specific heat capacity and a second output neuron indicative of heat conductivity.

The neural network also comprises a number of hidden layers 14, 19, each layer 14, 19 having a number of hidden neurons 15-18, 20-23. In some embodiments, the neural network comprises a single layer of hidden neurons. In some embodiments, the neural network comprises two layers 14, 19 of hidden neurons. The neurons can, by way of non-limiting example, have sigmoid and/or hyperbolic tangent and/or stepwise activation and/or rectified exponential linear unit functions. The neurons 15-18, 20-23 may be biased. The neural network 11 is ideally trained under test conditions. A series of measurements obtained under various test conditions is employed to train the network 11.

In some embodiments, the neural network 11 can, by way of example, be trained by a supervised training algorithm such as backpropagation. In some embodiments, the neural network 11 is trained using an evolutionary algorithm such as a genetic algorithm. The skilled artisan can actually combine training algorithms. A genetic algorithm can, by way of example, be employed to find a coarse estimate of the weights of the connections of the neural network 11. A backpropagation algorithm is then employed to further improve on the performance of the neural network 11.

After training the configuration of the neural network 11 and/or the weights of the connections of the neural network 11 are saved in a memory of or associated with the controller 7. The configuration of the neural network 11 and/or the weights of the connections of the neural network 11 as a whole then define a flow rate estimation and/or fluid classification scheme employed by the valve 1.

In some embodiments, a recurrent neural network is employed rather than the feed-forward network 11 shown on FIG. 5. Recurrent neural networks confer benefits in terms of factoring in historical values of dissipated heat and/or historical values of temperature.

In some embodiments, parts of the valve 1 or parts of a method incorporating teachings of the present disclosure can be embodied in hardware, in a software module executed by a processor, or by a cloud computer, or by a combination thereof. The software can include a firmware, a hardware driver run in the operating system, or an application program. Thus, the disclosure also relates to a computer program product for performing the operations presented herein. If implemented in software, the functions described can be stored as one or more instructions on a computer-readable medium. Some examples of storage media that can be used include random access memory (RAM), magnetic RAM, read only memory (ROM), flash memory, EPROM memory, EEPROM memory, registers, a hard disk, a removable disk, other optical disks, a Millipede® device, or any available media that can be accessed by a computer or any other IT equipment or appliance.

In some embodiments, a water-glycol mixture is a mixture of water and of ethylene glycol.

In some embodiments, the aforementioned controller (7) is configured to record and/or measure a quantity associated with controlling the heater (8), the recorded and/or measured quantity being selected from:
an amount of time required to attain and/or reach the temperature set point; or
an amount of energy required to attain and/or reach the temperature set point.

In some embodiments, the valve (1) comprises an anemometric sensor means (5; 5a; 5b; 8), the anemometric sensor means (5; 5a; 5b; 8) comprising:
the heater (8);
at least one of the first temperature transducer (5; 5a; 5b) or the second temperature transducer (5; 5b; 5a).

In some embodiments, the controller (7) comprises a clock, the controller (7) being configured to:
employ the clock to record and/or to estimate and/or to measure an amount of time required to attain and/or to reach the temperature set point;
the recorded and/or estimated and/or measured quantity being the recorded and/or estimated and/or measured amount of time.

In some embodiments, the controller (7) comprises a power meter, the controller (7) being configured to:
employ the power meter to record and/or to estimate and/or to measure an amount of energy required to attain and/or to reach the temperature set point;
the recorded and/or estimated and/or measured quantity being the recorded and/or estimated and/or measured amount of energy.

In some embodiments, the valve (1) comprises a power meter for recording and/or for estimating and/or for measuring power transmitted to the heater (8), the power meter being communicatively coupled to the controller (7), the controller (7) being configured to:
read an amount of energy required to attain and/or to reach the temperature set point from the power meter;
the recorded and/or estimated and/or measured quantity being the amount of energy read from the power meter.

The first temperature transducer (5; 5a; 5b) and the second temperature transducer (5; 5b; 5a) and the heater (8) may be arranged in the tempering circuit. In some embodiments, the valve (1) is a cooling or heating gauging device or a cooling or heating metering device.

In some embodiments, the controller (7) is configured to:
record and/or measure a quantity associated with controlling the heater (8), the recorded and/or measured quantity being indicative of and/or selected from:
an amount of time required to attain and/or to reach the temperature set point; or
an amount of energy required to attain and/or to reach the temperature set point; and
look up a type of mixture for the recorded and/or measured quantity and/or classify a fluid inside the fluid path (4) for the recorded and/or measured quantity.

In some embodiments, the controller (7) comprises a (non-volatile) memory storing a lookup table, the lookup table storing a plurality of values of recorded and/or measured quantities and a type of a mixture associated with at least one recorded and/or measured quantity. The lookup table can, in an embodiment, store a plurality of values of the recorded and/or measured quantity and a type of a water-glycol mixture or a type of a water-ethanol mixture associated with each recorded and/or measured quantity. The controller (7) can also comprise a (non-volatile) memory storing a lookup table, the lookup table storing a plurality of values of the first quantity and a type of a fluid in the fluid path (4) associated with at least one value of the first quantity. The controller (7) then uses the lookup table for classification.

In some embodiments, the controller (7) comprises a non-volatile memory storing a classification curve, the classification curve classifying a mixture and/or a type of a fluid in the fluid path (4) as a function of the first quantity, the controller (7) being configured to:
record a first quantity associated with controlling the heater (8) to attain the first temperature set point, the first quantity being indicative of:
an amount of time required to attain the first temperature set point; or
an amount of energy required to attain the first temperature set point; and
employ the classification curve to classify a (type of a) mixture and/or to classify a (type of a) fluid inside the fluid path (4) as a function of the first quantity.

In some embodiments, the classification curve is a graphical curve mapping values of the first quantity to types of mixtures and/or to types of fluids inside the fluid path (4). It is also envisaged that the classification curve is a mathematical relationship mapping values of the first quantity to types of mixtures and/or to types of fluids inside the fluid path (4).

In some embodiments, the controller (7) is configured to: read a feedback signal from the second temperature transducer (5; 5b; 5a) and control the heater (8) based on the feedback signal to attain and/or to reach the temperature set point at the second temperature transducer (5; 5b; 5a).

In some embodiments, the controller (7) is configured to:
produce a temperature set point;
read a feedback temperature signal from the second temperature transducer (5; 5b; 5a);
produce an error signal as a function of the temperature set point and of the feedback temperature signal;
produce a control output signal as a function of the error signal, the control output signal being indicative of and/or specifying and/or indicating an amount of energy to be dissipated by the heater (8); and
transmit the control output signal to the heater (8).

The controller (7) may be configured to produce the output signal using a set of proportional and integral parameters and/or a set of proportional and integral and derivative parameters. In an embodiment, the controller (7) employs self-adaptive control. That is, the control (7) functions to learn a set of proportional and integral parameters and/or functions to learn a set of proportional and integral and derivative parameters.

The controller (7) may be configured to calculate an error signal as a difference between the temperature set point and the feedback temperature signal. It is also envisaged that the controller (7) is configured to calculate an error signal as an absolute value of a difference between the temperature set point and the feedback temperature signal.

In some embodiments, the controller (7) comprises an output interface for data transmission to a remote controller;
the output interface being compatible with a predetermined communication bus protocol;
the controller (7) being configured to transmit the classified fluid and/or the estimated flow rate to the remote controller via the output interface using the predetermined communication bus protocol.

In some embodiments, the controller (7) comprises an input interface for receiving data from a remote controller;
the input interface being compatible with a predetermined communication bus protocol;
the controller (7) being configured to read details of a mixture comprising at least two liquids via the input interface using the predetermined communication bus protocol.

In some embodiments, the output interface is programmed with or is compatible with a predetermined communication bus protocol according to ISO 11898-1:2003 and/or according to IEEE 802.3ax, in particular according to 802.3af:2003 and/or according to 802.3at:2009 and/or according to 802.3bt:2017. The output interface can be programmed to be compatible with the predetermined communication bus protocol or provide hardware compatible with the predetermined communication bus protocol. The predetermined communication bus protocol is a digital protocol. In some embodiments, the output interface and/or the communication bus protocol enables encrypted communication between the controller (7) and the remote controller. A Diffie-Hellman key exchange procedure with or without elliptic curves can be employed to encrypt communication between the controller (7) and the remote controller. The remote controller may be installed in a location that is remote from the valve (1).

In some embodiments, the output interface is a wireless output interface. The output interface can be programmed to be compatible with the predetermined communication bus protocol for wireless communication or provide hardware compatible with the predetermined communication bus protocol for wireless communication.

In some embodiments, the output interface also functions to harvest energy. To that end, output interface can, by way of non-limiting example, rectify currents (electromagnetically) induced in an antenna (comprised by the interface). In some embodiments, the valve (1) comprises an energy buffer such as a (rechargeable) battery and stores energy harvested via the output interface in its energy buffer.

In some embodiments, the valve (1) comprises an output module communicatively coupled to the controller (7), wherein the controller (7) is configured to transmit the classified fluid and/or the flow rate to the output module; and wherein the output module comprises a display and is configured to produce information data on the classified fluid and/or on the estimated flow rate and to present the information data to an operator via the display.

In some embodiments, the output module visualizes the classified fluid and/or the estimated flow rate. The output module can, by way of non-limiting example, be a printer and/or a suitable display. The suitable display can, by way of non-limiting example, be a monochrome display, a grayscale display, or a color screen with suitable resolution. Suitable resolutions include, but are not limited to, 426×320 pixels, 470×320 pixels, 640×480 pixels, or 960×720 pixels etc. The display can, for instance, be a liquid crystal screen, a cathode ray tube monitor, or a screen made of organic light-emitting diodes.

The inlet temperature transducer (5a) is disposed at or near the inlet port (2) of the valve (1). The inlet temperature transducer (5a) may be disposed less than thirty millimeters, less than twenty millimeters, and/or less than ten millimeters from the inlet port (2). Small distances between the locations of the inlet temperature transducer (5a) and the inlet port (2) confer benefits in terms of accurate estimates of supply temperatures.

The outlet temperature transducer (5b) is disposed at or near the outlet port (3) of the valve (1). The outlet temperature transducer (5b) may be disposed less than thirty millimeters, less than twenty millimeters, and/or less than ten millimeters from the outlet port (3). Small distances between the locations of the outlet temperature transducer (5b) and the outlet port (3) confer benefits in terms of accurate estimates of return temperatures.

The second temperature transducer (5; 5b; 5a) may be disposed at a second location in the valve (1); the first temperature transducer (5; 5a; 5b) may be disposed at a first location in the valve (1); the first location being different from the second location.

In some embodiments, the first temperature transducer (5a; 5b) is different from the second temperature transducer (5b; 5a). In some embodiments, the first (5) and the second temperature transducers (5) are the same.

In some embodiments, to employ the first quantity to estimate and/or determine and/or calculate a specific heat capacity of a fluid inside the fluid path (4). In some embodiments, the first quantity and the second quantity are both employed to estimate a flow rate of the fluid through the fluid path (4). In some embodiments, the first quantity and the second quantity are both employed to classify a fluid inside the fluid path (4).

In some embodiments, the controller (7) is configured to employ the first quantity to determine a specific heat capacity of a fluid inside the fluid path (4) and to employ the second quantity to determine a flow rate such as a mass flow rate or a volume flow rate of the fluid through the fluid path (4). In some embodiments, the controller (7) is configured to employ the first quantity to calculate a specific heat capacity of a fluid inside fluid inside the fluid path (4) and to employ the second quantity to calculate a flow rate such as a mass flow rate or a volume flow rate of the fluid through the fluid path (4). In some embodiments, the controller (7) is configured to employ the first quantity to classify a fluid such as a water-glycol mixture inside fluid inside the fluid path (4) and to employ the second quantity to calculate a flow rate such as a mass flow rate or a volume flow rate of the fluid through the fluid path (4).

In some embodiments, the valve (1) is
a butterfly valve; or
a ball valve; or
a check valve; or
a plug valve such as a linear plug valve.

In some embodiments, the valve member (6) is selectively movable between a closed position which obturates flow of a fluid such as a mixture of two liquids (W, G) with different boiling points ($T_W$, $T_G$), in particular a water-glycol mixture, through the fluid path (4) and an open position which affords flow of a fluid such as a mixture of two liquids (W, G) with different boiling points ($T_W$, $T_G$) such as a water-glycol mixture through the fluid path (4).

In some embodiments, the flow rate through the fluid path (4) is a mass flow rate of a fluid such as a mixture of two liquids (W, G) with different boiling points ($T_W$, $T_G$), in particular a water-glycol mixture, through the fluid path (4). In some embodiments, the flow rate through the fluid path (4) is a volume flow rate of a fluid such as a mixture of two liquids (W, G) with different boiling points ($T_W$, $T_G$) such as a water-glycol mixture through the fluid path (4).

In some embodiments, the valve member (6) is selectively movable between a fully closed position which fully closes the fluid path (4) and a fully open position which fully opens the fluid path (4). In some embodiments, the close signal causes the valve actuator (9) to fully close the valve member (6) thereby fully closing the fluid path (4). In some embodiments, the open signal causes the valve actuator (9) to fully open the valve member (6) thereby fully opening the fluid path (4).

In some embodiments, the valve actuator (9) mechanically couples to the valve member (6). In some embodiments, a valve stem mechanically couples the valve actuator (9) and the valve member (6). In some embodiments, the valve (1) comprises a fluid channel and that the fluid channel comprises the fluid path (4). The fluid channel preferably extends between the inlet port (2) and the outlet port (3).

In some embodiments, the valve (1) comprising an inlet port (2) and an outlet port (3), wherein the fluid path (4) extends between the inlet port (2) and the outlet port (3). In some embodiments, the heater (8), the first temperature transducer (5; 5a; 5b), and the second temperature transducer (5; 5b;5a) are situated in the fluid path (4).

In some embodiments, the controller (7) is configured to produce the first temperature set point as a function of the first temperature signal by
producing a first reference temperature from the first temperature signal; and by
adding a first predetermined increment to the first reference temperature to produce the first temperature set point; and
wherein the controller (7) is configured to produce the second temperature set point as a function of the second temperature signal by
producing a second reference temperature from the second temperature signal; and by
adding a second predetermined increment to the second reference temperature to produce the second temperature set point.

In some embodiments, the first predetermined increment and the second predetermined increment are the same. In some embodiments, the first predetermined increment is different from the second predetermined increment. In some embodiments, the controller (7) has a memory such as a non-volatile memory and that the memory stores the first predetermined increment such as less than one Kelvin, less than two Kelvins, or less than five Kelvins and/or stores the second predetermined increment such as less than one Kelvin, less than two Kelvins or less than five Kelvins. Small increments mitigate scaling on a surface of the heater (8).

In some embodiments, the controller (7) is configured to:
record a first feedback signal from the second temperature transducer and control the heater (8) based on the first feedback signal to attain the first temperature set point at the second temperature transducer (5; 5b; 5a); and
after sending the open signal to the valve actuator (9):
record a second feedback signal from the second temperature transducer and control the heater (8) based on the second feedback signal to attain the second temperature set point at the second temperature transducer (5; 5b; 5a).

In some embodiments, the controller (7) is configured to:
record a first feedback temperature signal from the second temperature transducer (5; 5b; 5a);

produce a first error signal as a function of the first temperature set point and of the first feedback temperature signal;

produce a first control output signal as a function of the first error signal, the first control output signal being indicative of a first amount of energy to be dissipated by the heater (8);

transmit the first control output signal to the heater (8); and after sending the open signal to the valve actuator (9):

record a second feedback temperature signal from the second temperature transducer (5; 5b; 5a);

produce a second error signal as a function of the second temperature set point and of the second feedback temperature signal;

produce a second control output signal as a function of the second error signal, the second control output signal being indicative of a second amount of energy to be dissipated by the heater (8); and transmit the second control output signal to the heater (8).

In some embodiments, the controller (7) is configured to:

control the heater (8) to attain the first temperature set point at the second temperature transducer (5; 5b; 5a) by recording a first feedback signal from the second temperature transducer (5; 5b; 5a); and by producing a first feedback temperature from the first feedback signal; and by determining if the first feedback temperature is within a first predetermined margin from the first temperature set point;

if the first feedback temperature is within the first predetermined margin from the first temperature set point:

record a first quantity associated with controlling the heater (8), the first quantity being indicative of:

an amount of time required to attain the first temperature set point; or an amount of energy required to attain the first temperature set point; and after sending the open signal to the valve actuator (9):

control the heater (8) to attain the second temperature set point at the second temperature transducer (5; 5b; 5a) by recording a second feedback signal from the second temperature transducer (5; 5b; 5a); and by producing a second feedback temperature from the second feedback signal; and by determining if the second feedback temperature is within a second predetermined margin from the second temperature set point;

if the second feedback temperature is within the second predetermined margin from the second temperature set point:

record a second quantity associated with controlling the heater (8), the second quantity being indicative of:

an amount of time required to attain the second temperature set point; or an amount of energy required to attain the second temperature set point.

In some embodiments, the first predetermined margin and the second predetermined margin are the same. In some embodiments, the first predetermined margin is different from the second predetermined margin. In some embodiments, the controller (7) has a memory such as a non-volatile memory and that the memory stores the first predetermined margin such as less than one Kelvin, less than two Kelvins or less than five Kelvins and/or stores the second predetermined margin such as less than one Kelvin, less than two Kelvins or less than five Kelvins. Low margins yield small deviations from set points thereby affording accurate measurements.

In some embodiments, the controller (7) is configured to:

send a close signal to the valve actuator (9), the close signal causing the valve actuator (9) to close the valve member (6) thereby closing the fluid path (4); and at least one second after sending the close signal, record a first temperature signal from the first temperature transducer (5; 5a; 5b).

In some embodiments, the controller (7) is configured to:

send a close signal to the valve actuator (9), the close signal causing the valve actuator (9) to close the valve member (6) thereby closing the fluid path (4); and at least two seconds after sending the close signal, record a first temperature signal from the first temperature transducer (5; 5a; 5b).

In some embodiments, the controller (7) is configured to:

send a close signal to the valve actuator (9), the close signal causing the valve actuator (9) to close the valve member (6) thereby closing the fluid path (4); and at least five seconds after sending the close signal, record a first temperature signal from the first temperature transducer (5; 5a; 5b).

A delay between the close signal and any subsequent measurements of specific heat capacity allows remaining turbulence in the fluid path (4) to settle. Long delays yield improved measurement accuracy.

In some embodiments, the controller (7) comprises a timer such as a clock. The controller (7) is thus configured to:

send a close signal to the valve actuator (9), the close signal causing the valve actuator (9) to close the valve member (6) thereby closing the fluid path (4);

after sending the close signal, employ the timer of the controller (7) to wait for at least one second; and after waiting for at least one second, record a first temperature signal from the first temperature transducer (5; 5a; 5b).

In some embodiments, the controller (7) comprises a timer such as a clock. The controller (7) is thus configured to:

send a close signal to the valve actuator (9), the close signal causing the valve actuator (9) to close the valve member (6) thereby closing the fluid path (4);

after sending the close signal, employ the timer of the controller (7) to wait for at least two seconds; and after waiting for at least two seconds, record a first temperature signal from the first temperature transducer (5; 5a; 5b).

In some embodiments, the controller (7) comprises a timer such as a clock. The controller (7) is thus configured to:

send a close signal to the valve actuator (9), the close signal causing the valve actuator (9) to close the valve member (6) thereby closing the fluid path (4);

after sending the close signal, employ the timer of the controller (7) to wait for at least five seconds; and after waiting for at least five seconds, record a first temperature signal from the first temperature transducer (5; 5a; 5b).

A delay between the close signal and any subsequent measurements of specific heat capacity allows remaining turbulence in the fluid path (4) to settle. Long delays yield improved measurement accuracy.

In some embodiments, the controller (7) is configured to:

send a close signal to the valve actuator (9), the close signal causing the valve actuator (9) to close the valve member (6) thereby closing the fluid path (4);

receive a first confirmation signal from the valve actuator (9), the first confirmation signal indicating that the fluid path (4) is closed; and at least one second after receiving the first confirmation signal, record a first temperature signal from the first temperature transducer (5; 5a; 5b).

In some embodiments, the valve actuator (9) is configured to send and/or to transmit a first confirmation signal to the controller (7) upon completion of a close operation by the valve actuator (9). The valve actuator (9) according to a special aspect is configured to send and/or to transmit a first confirmation signal to the controller (7) when the valve controller (9) has completed closing the valve member (6). It is envisaged that the valve actuator (9) produces the first confirmation signal using a limit switch. The limit switch can, by way of non-limiting example, be affixed to a valve stem coupling the valve actuator (9) and the valve member (6). The limit switch can also be situated at a rotating part of the valve actuator (9) such as a rotor of an electric drive. The limit switch can further be situated at a stationary part of the valve actuator (9) such as a stator of an electric drive. It is also envisaged that the controller (7) is in operative communication with the limit switch.

In some embodiments, the controller (7) is configured to:
receive a first confirmation signal from the valve actuator (9), the first confirmation signal indicating that the fluid path (4) is closed; and at least two seconds after receiving the first confirmation signal, record a first temperature signal from the first temperature transducer (5; 5a; 5b).

In some embodiments, the controller (7) is configured to:
receive a first confirmation signal from the valve actuator (9), the first confirmation signal indicating that the fluid path (4) is closed; and at least five seconds after receiving the first confirmation signal, record a first temperature signal from the first temperature transducer (5; 5a; 5b).

In some embodiments, the controller (7) comprises a timer such as a clock. The controller (7) is thus configured to:
receive a first confirmation signal from the valve actuator (9), the first confirmation signal indicating that the fluid path (4) is closed;

in response to the first confirmation signal, employ the timer of the controller (7) to wait for at least one second; and after waiting for at least one second, record a first temperature signal from the first temperature transducer (5; 5a; 5b).

In some embodiments, the controller (7) comprises a timer such as a clock. The controller (7) is thus configured to:
receive a first confirmation signal from the valve actuator (9), the first confirmation signal indicating that the fluid path (4) is closed;

in response to the first confirmation signal, employ the timer of the controller (7) to wait for at least two seconds; and after waiting for at least two seconds, record a first temperature signal from the first temperature transducer (5; 5a; 5b).

In some embodiments, the controller (7) comprises a timer such as a clock. The controller (7) is thus configured to:
receive a first confirmation signal from the valve actuator (9), the first confirmation signal indicating that the fluid path (4) is closed;

in response to the first confirmation signal, employ the timer of the controller (7) to wait for at least five seconds; and after waiting for at least five seconds, record a first temperature signal from the first temperature transducer (5; 5a; 5b).

Confirmation of the closing operation prior to measurements of specific heat capacity inhibits flawed and/or inaccurate measurements due to partially open valve members (6).

In some embodiments, the controller (7) is configured to:
send an open signal to the valve actuator (9), the open signal causing the valve actuator (9) to open the valve member (6) thereby opening the fluid path (4); and at least one second after sending the open signal, record a second temperature signal from the first temperature transducer (5; 5a; 5b).

In some embodiments, the controller (7) is configured to:
send an open signal to the valve actuator (9), the open signal causing the valve actuator (9) to open the valve member (6) thereby opening the fluid path (4); and at least two seconds after sending the open signal, record a second temperature signal from the first temperature transducer (5; 5a; 5b).

In some embodiments, the controller (7) is configured to:
send an open signal to the valve actuator (9), the open signal causing the valve actuator (9) to open the valve member (6) thereby opening the fluid path (4); and at least five seconds after sending the open signal, record a second temperature signal from the first temperature transducer (5; 5a; 5b).

A delay between the open signal and any subsequent measurements of flow rate allows a flow rate through the fluid path (4) to attain stationary flow. Long delays yield improved measurement accuracy.

In some embodiments, the controller (7) comprises a timer such as a clock. The controller (7) is thus configured to:
send an open signal to the valve actuator (9), the open signal causing the valve actuator (9) to open the valve member (6) thereby opening the fluid path (4);

after sending the open signal, employ the timer of the controller (7) to wait for at least one second; and after waiting for at least one second, record a second temperature signal from the first temperature transducer (5; 5a; 5b).

In some embodiments, that the controller (7) comprises a timer such as a clock. The controller (7) is thus configured to:
send an open signal to the valve actuator (9), the open signal causing the valve actuator (9) to open the valve member (6) thereby opening the fluid path (4);

after sending the open signal, employ the timer of the controller (7) to wait for at least two seconds; and after waiting for at least two seconds, record a second temperature signal from the first temperature transducer (5; 5a; 5b).

In some embodiments, the controller (7) comprises a timer such as a clock. The controller (7) is thus configured to:
send an open signal to the valve actuator (9), the open signal causing the valve actuator (9) to open the valve member (6) thereby opening the fluid path (4);

after sending the open signal, employ the timer of the controller (7) to wait for at least five seconds; and after waiting for at least five seconds, record a second temperature signal from the first temperature transducer (5; 5a; 5b).

A delay between the open signal and any subsequent measurements of flow rate allows fluid flow through the fluid path (4) to attain stationary flow. Long delays yield improved measurement accuracy.

In some embodiments, the controller (7) is configured to:
send an open signal to the valve actuator (9), the open signal causing the valve actuator (9) to open the valve member (6) thereby opening the fluid path (4);
receive a second confirmation signal from the valve actuator (9), the second confirmation signal indicating that the fluid path (4) is open; and
at least one second after receiving the second confirmation signal, record a second temperature signal from the first temperature transducer (5; 5a; 5b).

In some embodiments, the valve actuator (9) is configured to send and/or to transmit a second confirmation signal to the controller (7) upon completion of an open operation by the valve actuator (9). The valve actuator (9) according to a special aspect is configured to send and/or to transmit a second confirmation signal to the controller (7) when the valve controller (9) has completed opening the valve member (6). It is envisaged that the valve actuator (9) produces the second confirmation signal using a limit switch. The limit switch can, by way of non-limiting example, be affixed to a valve stem coupling the valve actuator (9) and the valve member (6). The limit switch can also be situated at a rotating part of the valve actuator (9) such as a rotor of an electric drive. The limit switch can further be situated at a stationary part of the valve actuator (9) such as a stator of an electric drive. It is also envisaged that the controller (7) is in operative communication with the limit switch.

In some embodiments, the controller (7) is configured to:
send an open signal to the valve actuator (9), the open signal causing the valve actuator (9) to open the valve member (6) thereby opening the fluid path (4);
receive a second confirmation signal from the valve actuator (9), the second confirmation signal indicating that the fluid path (4) is open; and
at least two seconds after receiving the second confirmation signal, record a second temperature signal from the first temperature transducer (5; 5a; 5b).

In some embodiments, the controller (7) is configured to:
send an open signal to the valve actuator (9), the open signal causing the valve actuator (9) to open the valve member (6) thereby opening the fluid path (4);
receive a second confirmation signal from the valve actuator (9), the second confirmation signal indicating that the fluid path (4) is open; and
at least five seconds after receiving the second confirmation signal, record a second temperature signal from the first temperature transducer (5; 5a; 5b).

In some embodiments, the controller (7) comprises a timer such as a clock. The controller (7) is thus configured to:
send an open signal to the valve actuator (9), the open signal causing the valve actuator (9) to open the valve member (6) thereby opening the fluid path (4);
receive a second confirmation signal from the valve actuator (9), the second confirmation signal indicating that the fluid path (4) is open;
in response to the second confirmation signal, employ the timer of the controller (7) to wait for at least one second; and
after waiting for at least one second, record a second temperature signal from the first temperature transducer (5; 5a; 5b).

In some embodiments, the controller (7) comprises a timer such as a clock. The controller (7) is thus configured to:
send an open signal to the valve actuator (9), the open signal causing the valve actuator (9) to open the valve member (6) thereby opening the fluid path (4);
receive a second confirmation signal from the valve actuator (9), the second confirmation signal indicating that the fluid path (4) is open;
in response to the second confirmation signal, employ the timer of the controller (7) to wait for at least two seconds; and
after waiting for at least two seconds, record a second temperature signal from the first temperature transducer (5; 5a; 5b).

In some embodiments, the controller (7) comprises a timer such as a clock. The controller (7) is thus configured to:
send an open signal to the valve actuator (9), the open signal causing the valve actuator (9) to open the valve member (6) thereby opening the fluid path (4);
receive a second confirmation signal from the valve actuator (9), the second confirmation signal indicating that the fluid path (4) is open;
in response to the second confirmation signal, employ the timer of the controller (7) to wait for at least five seconds; and
after waiting for at least five seconds, record a second temperature signal from the first temperature transducer (5; 5a; 5b).

Confirmation of the open operation prior to measurements of flow rate inhibits flawed and/or inaccurate measurements due to partially closed valve members (6).

In some embodiments, the valve (1) comprises an inlet port (2) and an outlet port (3), the inlet port (2) and the outlet port (3) defining an upstream direction from the outlet port (3) to the inlet port (2);
the valve (1) further comprising a first thermoresistive device (10a) situated in the fluid path (4);
wherein the first thermoresistive device (10a) comprises a first housing and comprises the heater (8) and comprises the first temperature transducer (5a);
wherein the heater (8) and the first temperature transducer (5a) are situated inside the first housing; and
wherein the first thermoresistive device (10a) is situated upstream of the second temperature transducer (5b).

In some embodiments, the first housing is manufactured using additive manufacturing such as three-dimensional printing. Manufacture of the first housing can involve selective laser sintering.

In some embodiments, the controller (7) is in operative communication with the first thermoresistive device (10a). The first thermoresistive device (10a) may comprise a first resistive member. The first resistive member may form the heater (8) and forms the first temperature transducer (5a).

In some embodiments, the first resistive member is a resistor. The first resistive member can, by way of non-limiting examples, comprise an ohmic resistor and/or a positive thermal coefficient (PTC) resistor and/or a negative thermal coefficient (NTC) resistor.

In some embodiments, the valve (1) comprises an inlet port (2) and an outlet port (3), the inlet port (2) and the outlet port (3) defining a downstream direction from the inlet port (2) to the outlet port (3);

the valve (1) further comprising a second thermoresistive device (10b) situated in the fluid path (4);

wherein the second thermoresistive device (10b) comprises a second housing and comprises the heater (8) and comprises the second temperature transducer (5b);

wherein the heater (8) and the second temperature transducer (5b) are situated inside the second housing; and wherein the second thermoresistive device (10b) is situated downstream of the first temperature transducer (5a).

In some embodiments, the second housing is manufactured using additive manufacturing such as three-dimensional printing. Manufacture of the second housing can, in particular, involve selective laser sintering.

In some embodiments, the controller (7) is in operative communication with the second thermoresistive device (10b). The second thermoresistive device (10b) may comprise a second resistive member. The second resistive member may form the heater (8) and forms the second temperature transducer (5b).

In some embodiments, the second resistive member is a resistor. The second resistive member can, by way of non-limiting examples, comprise an ohmic resistor and/or a positive thermal coefficient (PTC) resistor and/or a negative thermal coefficient (NTC) resistor.

Some embodiments include a tangible machine-readable medium having a set of instructions stored thereon that when executed by one or more processors cause the one or more processors to perform any of the aforementioned methods. In some embodiments, the machine-readable medium is non-transitory.

It should be understood that the foregoing relates only to certain embodiments of the disclosure and that numerous changes can be made therein without departing from the scope of the disclosure as defined by the following claims. It should also be understood that the disclosure is not restricted to the illustrated embodiments and that various modifications can be made within the scope of the following claims.

REFERENCE NUMERALS 1 valve
2 inlet port
3 outlet port
4 fluid path
5, 5a, 5b temperature transducers
6 valve member
7 controller
8 heater
9 valve actuator
10a, 10b thermoresistive devices
11 neural network
12, 13 input neurons
14, 19 hidden layers
15-18 neurons
20-23 neurons
24 output neuron

The invention claimed is:

1. A valve comprising:
a controller;
a fluid path;
a valve member situated in the fluid path, the valve member movable between a closed position which obstructs the fluid path and an open position;
a valve actuator coupled to the valve member;
a heater downstream of the valve member;
a first temperature transducer downstream of the valve member; and
a second temperature transducer downstream of the valve member;
wherein the controller is in operative communication with the valve actuator, the heater, and the first and second temperature transducers, and the controller is configured to:
send a close signal to the valve actuator, causing the valve actuator to close the valve member;
record a first temperature signal from the first temperature transducer;
control the heater to attain a first temperature set point at the second temperature transducer;
record a first quantity associated with controlling the heater to attain the first temperature set point, the first quantity indicating at least one of: an amount of time required to attain the first temperature set point and an amount of energy required to attain the first temperature set point;
send an open signal to the valve actuator causing the valve actuator to open the valve member;
record a second temperature signal from the first temperature transducer;
control the heater to attain a second temperature set point at the second temperature transducer;
record a second quantity associated with controlling the heater to attain the second temperature set point, the second quantity indicating at least one of: an amount of time required to attain the second temperature set point, and an amount of energy required to attain the second temperature set point; and
employ the first quantity to classify a fluid inside and the second quantity to estimate a flow rate of the fluid through the fluid path;
wherein classifying the fluid includes identifying a particular mixture of components or a composition of the fluid.

2. The valve according to claim 1, further comprising an inlet port and an outlet port; wherein the fluid path extends from the inlet port to outlet port.

3. The valve according to claim 2, wherein the heater, the first temperature transducer, and the second temperature transducer are situated in the fluid path.

4. The valve according to claim 1, wherein:
the controller produces a first reference temperature based on the first temperature signal and adds a first predetermined increment to the first reference temperature to produce the first temperature set point; and
the controller produces a second reference temperature from the second temperature signal and adds a second predetermined increment to the second reference temperature to produce the second temperature set point.

5. The valve according to claim 1, wherein the controller is configured to:
record a first feedback signal from the second temperature transducer;
control the heater based on the first feedback signal to attain the first temperature set point at the second temperature transducer;

after sending the open signal to the valve actuator, record a second feedback signal from the second temperature transducer; and control the heater based on the second feedback signal to attain the second temperature set point at the second temperature transducer.

6. The valve according to claim 1, wherein the controller is configured to:

record a first feedback temperature signal from the second temperature transducer;

produce a first error signal as a function of the first temperature set point and the first feedback temperature signal;

produce a first control output signal as a function of the first error signal, the first control output signal indicative of a first amount of energy to be dissipated by the heater;

transmit the first control output signal to the heater;

after sending the open signal to the valve actuator, record a second feedback temperature signal from the second temperature transducer;

produce a second error signal as a function of the second temperature set point and the second feedback temperature signal;

produce a second control output signal as a function of the second error signal, the second control output signal indicative of a second amount of energy to be dissipated by the heater; and transmit the second control output signal to the heater.

7. The valve according to claim 1, wherein the controller is configured to:

record a first feedback signal from the second temperature transducer;

produce a first feedback temperature from the first feedback signal;

determine if the first feedback temperature is within a first predetermined margin from the first temperature set point;

if the first feedback temperature is within the first predetermined margin from the first temperature set point, record a first quantity associated with controlling the heater, the first quantity indicating: an amount of time required to attain the first temperature set point; or an amount of energy required to attain the first temperature set point;

after sending the open signal to the valve actuator, recording a second feedback signal from the second temperature transducer; producing a second feedback temperature from the second feedback signal; and determining if the second feedback temperature is within a second predetermined margin from the second temperature set point; and if the second feedback temperature is within the second predetermined margin from the second temperature set point, record a second quantity associated with controlling the heater, the second quantity indicating: an amount of time required to attain the second temperature set point; or an amount of energy required to attain the second temperature set point.

8. The valve according to claim 1, wherein the controller is configured to:

send a close signal to the valve actuator causing the valve actuator to close the valve member; and at least one second after sending the close signal, record a first temperature signal from the first temperature transducer.

9. The valve according to claim 1, wherein the controller is configured to:

send a close signal to the valve actuator causing the valve actuator to close the valve member;

receive a first confirmation signal from the valve actuator indicating that the fluid path is closed; and at least one second after receiving the first confirmation signal, record a temperature signal from the first temperature transducer.

10. The valve according to claim 1, wherein the controller is configured to:

send an open signal to the valve actuator causing the valve actuator to open the valve member; and at least one second after sending the open signal, record a temperature signal from the first temperature transducer.

11. The valve according to claim 1, wherein the controller is configured to:

send an open signal to the valve actuator causing the valve actuator to open the valve member;

receive a confirmation signal from the valve actuator indicating the fluid path is open; and at least one second after receiving the confirmation signal, record a temperature signal from the first temperature transducer.

12. The valve according to claim 1, further comprising:
an inlet port;
an outlet port downstream of the inlet port; and
a first thermoresistive device situated in the fluid path;
wherein the first thermoresistive device comprises a first housing and the heater and the first temperature transducer;
wherein the heater and the first temperature transducer are situated inside the first housing; and
wherein the first thermoresistive device is situated upstream of the second temperature transducer.

13. The valve according to claim 1, further comprising:
an inlet port;
an outlet port downstream of the inlet port; and
a second thermoresistive device situated in the fluid path;
wherein the second thermoresistive device comprises a second housing and the heater and the second temperature transducer;
wherein the heater and the second temperature transducer are situated inside the second housing; and
wherein the second thermoresistive device is situated downstream of the first temperature transducer.

14. A method for determining parameters of a fluid, the method comprising:

sending a close signal to a valve actuator of a valve, the close signal causing the valve actuator to close a valve member situated in a fluid path of the valve thereby closing the fluid path;

recording a first temperature signal from a first temperature transducer situated in the fluid path downstream of the valve member;

controlling a heater in the fluid path downstream of the valve member to attain a first temperature set point at a second temperature transducer situated in the fluid path downstream of the valve member;

recording a first quantity associated with controlling the heater to attain the first temperature set point, the first quantity indicating: an amount of time required to attain the first temperature set point; or an amount of energy required to attain the first temperature set point; and sending an open signal to the valve actuator causing the valve actuator to open the valve member;
recording a second temperature signal from the first temperature transducer;
controlling the heater to attain a second temperature set point at the second temperature transducer;
recording a second quantity associated with controlling the heater to attain the second temperature set point, the second quantity indicating: an amount of time required to attain the second temperature set point; or an amount of energy required to attain the second temperature set point; and
employing the first quantity to classify the fluid inside the fluid path and employing the second quantity to estimate a flow rate of the fluid through the fluid path;
wherein classifying the fluid includes identifying a particular mixture of components or a composition of the fluid.

* * * * *